(12) United States Patent
Proost et al.

(10) Patent No.: US 6,977,071 B2
(45) Date of Patent: Dec. 20, 2005

(54) AMINO-TERMINALLY TRUNCATED RANTES AS CHEMOKINE ANTAGONISTS

(75) Inventors: Paul Proost, Heverlee-Leuven (BE); Sofie Struyf, Rumst (BE); Jo Van Damme, Brussells (BE)

(73) Assignee: Applied Research Systems ARS Holding NV, Curacao (AN)

( * ) Notice: Subject to any disclaimer, the term of this patent is extended or adjusted under 35 U.S.C. 154(b) by 0 days.

(21) Appl. No.: 09/537,858

(22) Filed: Mar. 28, 2000

(65) Prior Publication Data

US 2003/0119148 A1 Jun. 26, 2003

Related U.S. Application Data

(63) Continuation of application No. PCT/EP98/06143, filed on Sep. 28, 1998.

(30) Foreign Application Priority Data

| Sep. 29, 1997 | (EP) | 97116863 |
| Dec. 19, 1997 | (EP) | 97122471 |
| Mar. 10, 1998 | (EP) | 98104216 |

(51) Int. Cl.[7] .................. C07K 14/52; A61K 38/19
(52) U.S. Cl. .................. 424/85.1; 530/324; 514/2; 514/8; 514/12; 514/885
(58) Field of Search .................. 514/2, 8, 12, 885; 424/85.1; 530/324

(56) References Cited

U.S. PATENT DOCUMENTS

5,739,103 A * 4/1998 Rollins et al.
6,168,784 B1 * 1/2001 Offord et al.

FOREIGN PATENT DOCUMENTS

WO  WO 96/17935  6/1996

OTHER PUBLICATIONS

Noso et al J. Immunol. 1996; 156: 1946–1953.*
Sozzani et al., *Journal of Immunology*, 152:3615–3622 (1994).
Proudfoot et al., *Journal of Biological Chemistry*, 271(5):2599–2603 (1996).
Proost et al., *Biochemistry*, 32 10170–10177 (1993).
Proost et al., *Journal of Immunology*, 150:1000–1010, No. 3 (1993).
Proost et al., *METHODS: A Companion to Methods in Enzymology*, 10:82–92 (1996).
Proost et al., *Cytokine*, 7(2):97–104 (1995).
Grynkiewicz et al., *Journal of Biological Chemistry*, 260(6):3440–3450 (1985).
De Meester et al., *Journal of Immunological Methods*, 189:99–105 (1996).
Clark–Lewis et al., *Journal of Biological Chemistry* 266(34:23128–23134 (1991).
Baggiolini et al., *Ann. Rev. Immunol.*, 15:675–705 (1997).
Baggiolini et al., *Advances in Immunology*, 55:97–179 (1994).
Van Damme, et al., *J. Exp. Med.*, 176:59–65 (1992).
Arenzana–Selsdedis et al., *Nature*, 383: 400 (1996).
Gong et al., *Journal of Biological Chemistry*, 271(18) 10521–10527 (1996).
Gong et al., *J. Exp. Med.*, 181:631–640 (1995).
Van Damme et al., *Eur. J. Immunol.*, 20:2113–2118 (1990).
Van Damme et al., *Eur. J. Biochem.*, 181,:337–344 (1989).
Van Coillie et al., *Biochemical and Biophysical Research Communications*, 231:726–730 (1997).
Oravecz et al., *Journal of Experimental Medicine*, 186(11): 1865–1872 (1997).
Schall et al., *Journal of Immunology*, 41(3):1018–1025 (1998).
Schols et al., *J. Exp. Med.*, 186(8):1383–1388 (1997).
Deng et al., *Nature*, 381:661–666 (1996).
Wuyts et al., *Biochemistry*, 36:2716–2723 (1997).
Taub., *Cytokine & Growth Factor Reviews*, 7(4):355–376 (1996).
Watz et al., *Biochemical and Biophysical Research Communications*, 159(3):969–975 (1989).

* cited by examiner

*Primary Examiner*—Prema Mertz
(74) *Attorney, Agent, or Firm*—Browdy and Neimark, PLLC

(57) ABSTRACT

The present invention relates to amino-terminally truncated RANTES, lacking $NH_2$-terminal amino acids corresponding to amino acid residues 1, 1–2, 1–3 or 1–4 of the naturally-occurring RANTES and having chemokine antagonistic activity, as well as cDNA sequences encoding them, their use in therapy and/or in diagnosis of the diseases, in which an antagonistic activity of the chemokine effects is required, and pharmaceutical compositions comprising them.

4 Claims, 9 Drawing Sheets

RANTES
-23
MKVSAARLAV ILIATALCAP ASASPYSSDT TPCCFAYIAR PLPRAHIKEY FYTSGKCSNP
AVVFVTRKNR QVCANPEKKW VREYINSLEM S
                                 68

FIG. 1

SEQUENCE LISTING

<160> NUMBER OF SEQ ID NOS: 2

<210> SEQ ID NO 1
<211> LENGTH: 91
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Met Lys Val Ser Ala Ala Arg Leu Ala Val Ile Leu Ile Ala Thr Ala
 1               5                  10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
 65                 70                  75                  80

Val Arg Glu Tyr Ile Asn Ser Leu Glu Met Ser
                85                  90

<210> SEQ ID NO 2
<211> LENGTH: 66
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Tyr Ser Ser Asp Thr Thr Pro Cys Cys Phe Ala Tyr Ile Ala Arg Pro

-continued

```
 1               5                  10                 15
Leu Pro Arg Ala His Ile Lys Glu Tyr Phe Tyr Thr Ser Gly Lys Cys
            20                  25                 30

Ser Asn Pro Ala Val Val Phe Val Thr Arg Lys Asn Arg Gln Val Cys
        35                  40                 45

Ala Asn Pro Glu Lys Lys Trp Val Arg Glu Tyr Ile Asn Ser Leu Glu
    50                  55                  60

Met Ser
65
```

AMINO-TERMINALLY TRUNCATED RANTES AS CHEMOKINE ANTAGONISTS

This application is a continuation of copending application(s) International Application PCT/EP98/06143 filed on 28 Sep. 1998 and which designated the U.S.

FIELD OF THE INVENTION

The present invention relates to amino-terminally truncated RANTES, lacking $NH_2$-terminal amino acids corresponding to amino acid residues 1, 1–2, 1–3 or 1–4 of the naturally-occurring RANTES and having chemokine antagonistic activity, as well as cDNA sequences encoding them, their use in therapy and/or in diagnosis of the diseases, in which an antagonistic activity of the chemokine effects is required, and pharmaceutical compositions comprising them.

BACKGROUND OF THE INVENTION

Chemokines constitute a family of small pro-inflammatory cytokines with leukocyte chemotactic and activating properties. Depending on the position of the first cysteines, the chemokine family can be divided in C—C, C—X—C and C—$X_3$—C chemokines (Baggiolni M. et al., 1994; Baggiolini M. et al., 1997 and Taub D. et al., 1996).

Many C—X—C chemokines such as interleukin-8 (IL-8) are chemotactic for neutrophils, while C—C chemokines, such as monocyte chemotactic protein-3 (MCP-3), are active on a variety of leukocytes including monocytes, lymphocytes, eosinophils, basophils, NK cells and dendritic cells.

The $NH_2$ terminal domain of chemokines is involved in receptor-binding and $NH_2$-terminal processing can activate chemokines, reduce their chemokine activity or render chemokines completely inactive.

The C—X—C chemokine platelet basic protein becomes a neutrophil chemotactic peptide (NAP-2) only after removal of the 24 $NH_2$-terminal residues (Walz A. et al., 1989 and Van Damme J. et al., 1990).

Deletion of up to 8 $NH_2$-terminal residues from IL-8 results in an enhanced chemotactic activity, but further cleavage of the Glu-Leu-Arg motif, which is located in front of the first Cys in all neutrophil chemotactic C—X—C chemokines, causes complete inactivation (Clark-Lewis I. et al., 1991).

Similar $NH_2$-terminal proteolysis (up to 8 amino acids) of another C—X—C chemokine, granulocyte chemotactic protein-2 (GCP-2), has no effect on the neutrophil chemotactic activity (Proost P. et al, 1993a).

RANTES (is an acronym for "Regulated upon Activation, Normally T Expressed, and presumably Secreted") is a C—C chemokine, whose cDNA clone has been isolated from a cDNA library enriched for T cell-specific sequences (Schall T. J. et al., 1988).

The synthetical C—C chemokines MCP-1, MCP-3 and RANTES missing the 8 to 9 $NH_2$-terminal amino acids are inactive on monocytes and are useful as receptor antagonists (Gong J. et al., 1996; and Gong J. et al., 1995).

Extension of RANTES with one methionine results in complete inactivation of the molecule and Met-RANTES behaves as an antagonist for the authentic RANTES (Proudfoot A. E. et al., 1996).

DESCRIPTION OF THE INVENTION

The main object of the present invention is amino-terminally truncated RANTES, lacking $NH_2$-terminal amino acids corresponding to amino acid residues 1, 1–2, 1–3 or 1–4 of the naturally-occurring RANTES and having chemokine antagonistic activity.

A particular object of the present invention is RANTES (3–68), which is RANTES lacking the first 2 amino acids, as shown in FIG. 1 and in SEQ ID NO: 2.

The amino-terminally truncated RANTES of the invention can be in a glycosylated or non-glycosylated form.

The term "chemokine antagonist" means 'which acts as antagonist to the mature full-length naturally-occurring chemokines'.

Another object of the invention are the DNA molecules comprising the DNA sequences coding for the amino-terminally truncated RANTES of the invention, including nucleotide sequences substantially the same. The cDNA sequence of intact RANTES is disclosed in Schall T. J. et al. (1988) and the cDNA of the truncated RANTES can be easily deduced.

"Nucleotide sequences substantially the same" includes all other nucleic acid sequences which, by virtue of the degeneracy of the genetic code, also code for the given amino acid sequences.

The invention also includes expression vectors which comprise the above DNAs, host-cells transformed with such vectors and a process of preparation of such amino-terminally truncated RANTES of the invention, through the culture in appropriate culture media of said transformed cells.

The DNA sequence coding for the proteins of the invention can be inserted and ligated into a suitable plasmid. Once formed, the expression vector is introduced into a suitable host cell, which then expresses the vector(s) to yield the desired protein.

Expression of any of the recombinant proteins of the invention as mentioned herein can be effected in eukaryotic cells (e.g. yeasts, insect or mammalian cells) or prokaryotic cells, using the appropriate expression vectors. Any method known in the art can be employed.

For example the DNA molecules coding for the proteins obtained by any of the above methods are inserted into appropriately constructed expression vectors by techniques well known in the art (see Sambrook et al, 1989). Double stranded cDNA is linked to plasmid vectors by homopolymeric tailing or by restriction linking involving the use of synthetic DNA linkers or blunt-ended ligation techniques: DNA ligases are used to ligate the DNA molecules and undesirable joining is avoided by treatment with alkaline phosphatase.

In order to be capable of expressing the desired protein, an expression vector should also comprise specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the protein of the invention is inserted into vector(s), having the operably linked transcriptional and translational regulatory signals, which is capable of integrating the desired gene sequences into the host cell.

The cells which have been stably transformed by the introduced DNA can be selected by also introducing one or more markers which allow for selection of host cells which contain the expression vector. The marker may also provide for phototrophy to a auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Factors of importance in selecting a particular plasmid or viral vector include: the ease with which recipient cells, that contain the vector may be recognized and selected from those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA construct(s) may be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Preferred are eukaryotic hosts, e.g. mammalian cells, such as human, monkey, mouse, and Chinese hamster ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector(s), the host cells are grown in a selective medium, which selects for the growth of vector-containing cells. Expression of the cloned gene sequence(s) results in the production of the desired proteins.

The amino-terminally truncated RANTES of the invention may be prepared by any other well known procedure in the art, in particular, by the well established chemical synthesis procedures, utilizing automated solid-phase peptide synthesizers followed by chromatographic purification.

The chemokines of the invention may, for example, be synthesized by Fmoc (9-fluorenylmethoxycarbonyl), tBoc (t-butoxycarbonyl) or any other comparable chemical synthesis with or without appropriate side-chain protection groups on the different amino acids. The amino acids with or without appropriate side-chain protection groups are preactivated—e.g. with HBTU/HOBt [2-(1H-Benzotriazole-1yl)-1,1,3,3-tetramethyl-uromium hexafluorophosphate/1-hydroxybenzotriazole)—and coupled to the growing peptide chain. Before the addition of the following residue, the protection group (e.g. Fmoc) is removed from the α-amino group. After synthesis, all protection groups are removed, the intact full length peptides are purified and chemically or enzymatically folded (including the formation of disulphide bridges between cysteines) into the corresponding chemokines of the invention.

Purification of the natural, synthetic or recombinant proteins is carried out by any one of the methods known for this purpose, i.e. any conventional procedure involving extraction, precipitation, chromatography, electrophoresis, or the like (see for example Proost P. et al., 1996). A further purification procedure that may be used in preference for purifying the protein of the invention is affinity chromatography using monoclonal antibodies, or affinity for heparin, which bind the target protein and which are produced and immobilized on a gel matrix contained within a column. Impure preparations containing the proteins are passed through the column. The protein will be bound to the column by the specific antibody while the impurities will pass through. After washing, the protein is eluted from the gel by a change in pH or ionic strength.

The amino-terminally truncated RANTES of the invention are useful in the therapy and/or diagnosis of the diseases, in which an antagonistic activity of the chemokine effects is required. Examples of such diseases include: inflammatory diseases, angiogenesis- and hematopoiesis-related diseases, tumors, infectious diseases, including HIV, auto-immune diseases, atherosclerosis, pulmonary diseases and skin disorders. The preferred use is in the field of HIV-infection.

Therefore, in a further aspect, the present invention provides the use of the protein of the invention in the manufacture of a medicament for the treatment of the above-mentioned diseases.

The medicament is preferably presented in the form of a pharmaceutical composition comprising the proteins of the invention together with one or more pharmaceutically acceptable carriers and/or excipients. Such pharmaceutical compositions form yet a further aspect of the present invention.

A further embodiment of the invention is the method of treatment of the above-mentioned diseases comprising administering a pharmacologically active amount of the amino-terminally truncated RANTES of the invention to subjects at risk of developing such diseases or to subjects already showing such pathologies.

It has also been found that CD26/DPP IV is able to generate $NH_2$-terminally truncated RANTES in vitro. RANTES is the first cytokine reported whose biological activity can be modified by CD26/DPP IV.

Therefore, another object of the present invention is the use of CD26/DPP IV in the therapy and/or diagnosis of the diseases, in which an antagonistic activity of the chemokine effects is required, with particular focus on inflammatory, immune and infectious diseases.

Since this represents the first example of an identified mechanism for endogeneously regulated chemokine modification into an antagonist, similar physiological processing, but mediated by other factors (proteases). The use of such factors (proteases) in the therapy and/or diagnosis of the above diseases is also included in this invention.

The invention will now be described by means of the following Examples, which should not be construed as in any way limiting the present invention. The Examples will refer to the Figures specified here below.

DESCRIPTION OF THE FIGURES

FIG. 1: it shows the amino acid sequence of RANTES (SEQ ID NO. 1). Signal sequences are reported in italics, whereas C-residues are in bold. Arrows indicate the first amino acids of the amino-terminally truncated RANTES of the invention, also called RANTES(3–68).

EXAMPLES

Example 1

Amino-terminally Truncated RANTES

Material and Methods

Reagents

Figure 2:
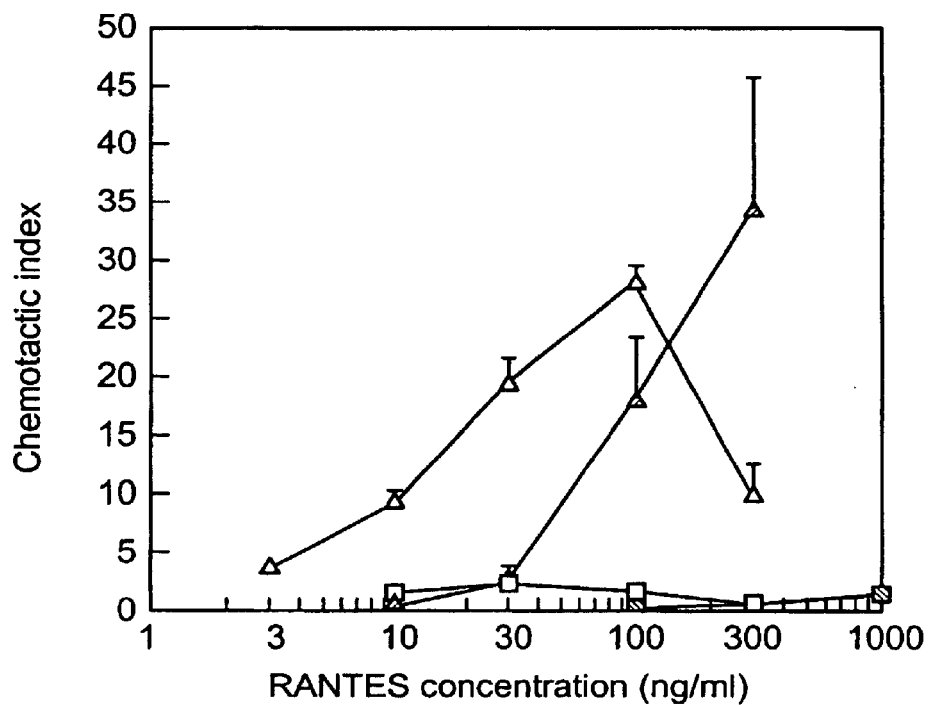
FIG. 2: The chemotactic potencies of intact and $NH_2$-terminally truncated forms of natural or recombinant RANTES for monocytic THP-1 cells were compared in the Boyden microchamber assay: Natural RANTES(1–68) (△), natural, truncated RANTES(3–68) (□), intact recombinant RANTES(1–68) (▲) and CD26/DPP IV cleaved recombinant RANTES(3–68) (■). Results represent the mean chemotactic index±SEM of four or more independent experiments.

Natural human RANTES was produced by human Malavu hepatosarcoma cells, MG-63 osteosarcoma cells or peripheral blood leukocytes (Blood transfusion centers of Antwerp and Leuven) and purified as previously described (Proost P. et al., 1996 and Proost P. et al., 1993). MCP-2, MCP-3 and GCP-2 were synthesized by Fmoc chemistry (Proost P. et al., 1995 and Wuyts A. et al., 1997), recombinant human RANTES was obtained from Peprotech (Rocky Hill, N.J.) and recombinant MCP-1 was a gift from Dr. J. J. Oppenheim (NCI-NIH, Frederick, Md.).

Human osteosarcoma (HOS) cells transfected with CD4 and one of the CC chemokine receptors CCR1, CCR3 or CCR5 (Deng H., et al., 1996) were grown in DMEM with glutamax. Puromycin (1 μg/ml) was added to the medium as a selection agent. All growth media (Gibco BRL/Life Technologies, Paisley, UK) were enriched with 10% FCS.

Human CD26/DPP IV was obtained from prostasomes, prostate derived organelles, which occur freely in seminal plasma. The enzyme was purified to homogeneity as described before using ion exchange followed by affinity chromatography onto adenosine deaminase (De Meester I. et al., 1996).

Incubation of Chemokines with CD26/DPP IV and Detection of Proteolytic Processing A 100 to 1000 molar excess of chemokine was incubated overnight with CD26/DPP IV in 100 mM Tris/HCl pH 7.7. Chemokines were separated from CD26/DPP IV by SDS-PAGE on a Tris/Tricine gel system as previously described (Proost P. et al., 1996).

Proteins were electroblotted on PVDF (polyvinylidene fluoride) membranes (Problott, Perkin Elmer, Foster City, Calif.) and stained with coomassie brilliant blue R250. After destaining, membranes were rinsed at least 5 times with ultrapure water (Milli Q; Millipore, Bedford, Mass.).

To obtain sufficient amounts of pure truncated chemokine for biological assays, about 50 µg of recombinant chemokine was treated with CD26/DPP IV and the cleavage product was acidified with 0.1% trifluoroacetic acid (TFA). Tween 20 (0.01%) was added to prevent the chemokines from sticking to the tubes.

Chemokines were separated from CD26/DPP IV in an acetonitrile gradient on a C-8 Aquapore RP-300 column (1×50 mm) (Perkin Elmer). Fractions containing proteins were analyzed by SDS-PAGE and silver stained as described.

CD26/DPP IV treated chemokines, purified by RP-HPLC or excised from PVDF blots, were $NH_2$-terminally sequenced by Edman degradation on a pulsed liquid phase 477A/120A protein sequencer (Perkin Elmer) using N-methylpiperidine as a coupling base.

Defection of Chemotactic Activity

Chemokines were tested for their chemotactic potency on freshly isolated peripheral blood neutrophilic granulocytes ($10^6$ cells/ml) or cultured monocytic THP-1 cells ($0.5×10^6$ cells/ml) in the Boyden microchamber (Proost P. et al., 1996 and Proost P. et al., 1993).

After 45 min (granulocytes) or 2 h (THP-1 cells) incubation at 37° C., the cells were fixed and stained. The cells that migrated through the 5 µm pore size polycarbonate membranes were counted microscopically in ten oil immersion fields.

The chemotactic index (C.I.) of a sample (triplicates in each chamber) was calculated as the number of cells that migrated to the test sample divided by the number of cells that migrated to control medium. In desensitization experiments, cells were incubated with biologically inactive chemokine-variants for 10 min at 37° C. before transfer to the chamber.

The percentage inhibition of the C.I. obtained by desensitization with HBSS-treated control cells was calculated for the evaluation of chemotaxis desensitization.

Detection of Intracellular $Ca^{2+}$ Concentrations

Intracellular $Ca^{2+}$ concentrations ($[Ca^{2+}]_i$) were measured as previously described (Wuyts A., et al., 1997). Briefly, purified cells were incubated with the fluorescent indicator fura-2 (2.5 µM fura-2/AM, Molecular Probes Europe BV, Leiden, The Netherlands) and 0.01% Pluronic F-127 (Sigma, St. Louis, Mo.).

After 30 min, cells were washed twice, resuspended in HBSS with 1 mM $Ca^{2+}$ and incubated for 10 min at 37° C. before fura-2 fluorescence was measured in an LS50B luminescence spectrophotometer (Perkin Elmer). Upon excitation at 340 and 380 nm, fluorescence was detected at 510 nm. The $[Ca^{2+}]_i$ was calculated from the Grynkiewicz equation (Grynkiewicz G. et al., 1985).

In order to determine $R_{max}$, the cells were lysed with 50 µM digitonin. Subsequently, the pH was adjusted to 8.5 with 20 mM Tris and $R_{min}$ was obtained by addition of 10 mM EGTA to the lysed cells. The $K_d$ used for calibration was 224 nM. For desensitization experiments, cells were first stimulated with buffer or chemokine at different concentrations. As a second stimulus, chemokines were added at a concentration inducing a significant increase in the $[Ca^{2+}]_i$ after prestimulation with buffer. The percentage inhibition of the $[Ca^{2+}]_i$-increase in response to the second stimulus by prestimulation of the cells was calculated.

Inhibition of HIV-1 Infection

The HIV-1 M-tropic strains BaL and SF162 were obtained through the MRC AIDS reagent project (Herts, UK). Peripheral blood mononuclear cells (PBMC) from healthy donors were isolated by density gradient centrifugation (5,23) and stimulated with PHA at 1 µg/ml (Sigma, Bomem, Belgium) for 3 days at 37° C. The activated cells (PHA-stimulated blasts) were washed three times with PBS, and infected with a virus as described previously (Schols D. et al., 1997). HIV-1 infected or mock-infected PHA-stimulated blasts were cultured in the presence of 25 U/ml of IL-2 and varying concentrations of RANTES (1–68) or RANTES (3–68). Cell supernatant was collected at day 10 and HIV-1 core antigen in the supernatant was analysed by a p-24 Ag ELISA kit (DuPont/NEN Life Science Products, Brussels, Belgium).

Results

Identification and Biological Characterization of Natural, $NH_2$-terminally Truncated RANTES A different $NH_2$-terminally truncated form of human GCP-2 has been previously isolated (Proost P. et al., 1993). The least truncated GCP-2-form was cleaved beyond Pro at the penultimate position [GCP-2(3–75)]. Using a similar standard purification procedure, the C—C chemokine RANTES was purified from peripheral blood leukocytes or sarcoma cells (Proost P. et al., 1996).

In particular, conditioned media from MG-63 or Malavu sarcoma cells induced with a cytokine mixture were fractionated to isolate natural chemokine variants. The chemokines were purified by subsequent antibody or heparin affinity chromatography, cation-exchange chromatography (mono S FPLC) and RP-BPLC, and immunoreactive forms were detected by specific chemokine ELISAs. On the cation-exchange column, IL-8 was found to elute in close proximity of RANTES (between 0.7 and 0.75 M NaCl). Nevertheless, both chemokines were separated from each other by RP-BPLC (RANTES and IL-8 eluting at 27.5% and 30% acetonitrile, respectively). Amino acid sequence analysis of the pure proteins confirmed that IL-8 occured in different $NH_2$-terminally truncated forms, which were previously isolated on the basis of their chemotactic activity (Van Damme J. et al., 1989). However, for RANTES only one single form was isolated, which was missing two $NH_2$-terminal residues compared to intact RANTES. In view of its predominant appearance, this RANTES(3–68) was analyzed in more detail to verify its chemotactic activity for monocytes and eosinophils. In particular, RANTES(3–68)

was tested for chemotactic and/or intracellular $Ca^{2+}$-releasing activity and their biological potency was compared with that of the respective intact chemokines.

Figure 3:
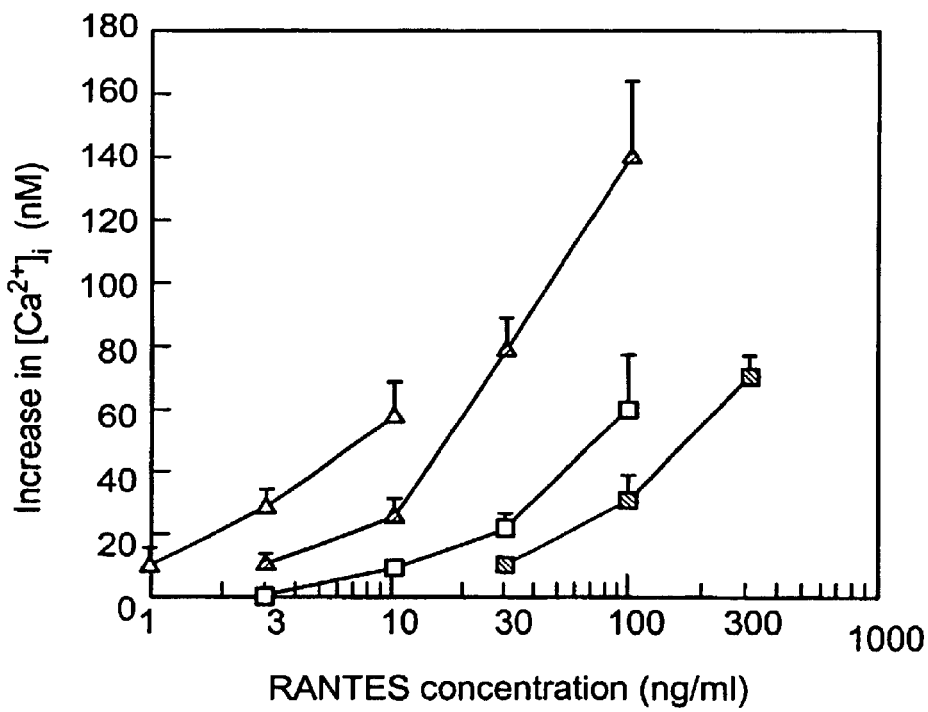
FIG. 3: Effect of natural RANTES(3–68) (□), natural RANTES(1–68) (△), recombinant RANTES(1–68) (▲) and recombinant CD26/DPP IV treated RANTES(3–68) (■) on the $[Ca^{2+}]_i$ in THP-1 cells. Results represent the mean increase in $[Ca^{2+}]_i$±SEM of three or more independent experiments.

$NH_2$-terminal deletion of two residues from RANTES resulted in considerably decreased monocyte chemotactic and $Ca^{2+}$-releasing activities. Compared to intact natural RANTES (minimal effective dose of 3–10 ng/ml), natural RANTES(3–68) was totally inactive when tested at concentrations as high as 300 ng/ml in the Boyden microchamber (FIG. 2). In addition, 10 times higher concentrations of natural RANTES(3–68), compared to RANTES(1–68), were necessary to obtain a similar $Ca^{2+}$-response (FIG. 3).

CD26/DPP IV Removes the $NH_2$-terminal Dipeptides of Chemokines

In order to investigate whether the aminopeptidase CD26/DPP IV could be responsible for the $NH_2$-terminal truncation of RANTES, the intact chemokine was incubated overnight with CD26/DPP IV, blotted to PVDF membranes, stained with Coomassie blue and subjected to automatic Edman degradation. CD26/DPP IV treatment of RANTES resulted in the removal of the $NH_2$-terminal dipeptides. Parallel incubation of chemokine with buffer without CD26/DPP IV had no effect.

Since other chemokines contained the consensus sequence for CD26/DPP IV cleavage and since the $NH_2$-terminus of MCPs was shown to be crucial for biological activity (Gong J. et al., 1996 and Gong J. et al., 1995), MCP-1, MCP-2 and MCP-3 were also incubated with CD26/DPP IV.

After treatment, MCPs were blotted on PVDF membranes and Coomassie blue stained to confirm that a sufficient amount of protein was recovered for Edman degradation. However, no $NH_2$-terminal sequence could be detected, indicating that CD26/DPP IV does not alter the $NH_2$-terminus of MCPs which is blocked for Edman degradation by a pyroglutamic acid.

Comparison of the Biological Activity of Intact and CD26IDPP IV-treated RANTES

Similar to natural RANTES(3–68), C-8 RP-HPLC purified, CD26/DPP IV-treated recombinant RANTES was inactive in Boyden microchamber chemotaxis experiments when used at concentrations up to 1 µg/ml, while a significant monocyte chemotactic response was detected with intact recombinant RANTES from 30 to 100 ng/ml onwards (FIG. 2).

When the truncation effect was tested in the $Ca^{2+}$-mobilization assay, RANTES(3–68) induced a low but significant increase at 100 ng/ml. Intact RANTES, however, was already active at 10 ng/ml (FIG. 3). In conclusion, although only two $NH_2$-terminal residues were removed, the monocyte chemotactic and $Ca^{2+}$-mobilizing potency of RANTES decreased 10 to 100-fold.

RANTES(3–68) is a Natural Chemotaxis Antagonist for Intact RANTES

In view of the inactivity of RANTES(3–68) in monocyte chemotaxis experiments, we tested whether this truncated RANTES might act as an antagonist. RANTES(3–68), at 1 µg/ml, almost completely (82%) desensitized for the chemotactic effect of 100 ng/ml of intact RANTES (Table I).

When a 3-fold excess of RANTES(3–68) was added to the upper well, chemotaxis of THP-1 cells towards intact RANTES was inhibited by about 50–70%. RANTES(3–68) at 300 ng/ml could still inhibit about 30% of the chemotactic response towards an equal concentration of intact RANTES.

Figure 4:
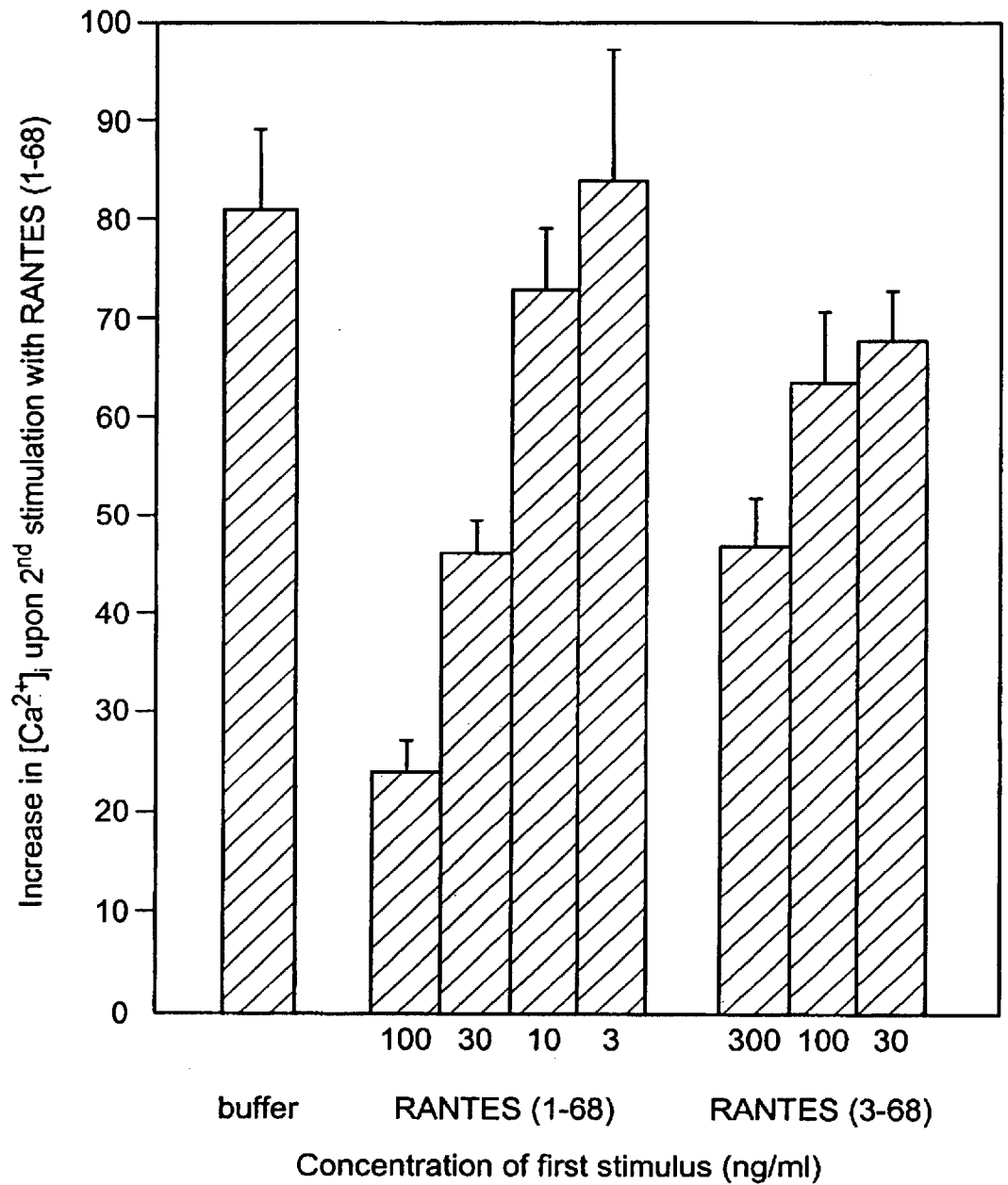
FIG. 4: It shows the desensitization of the $Ca^{2+}$-mobilizing activity of intact recRANTES(1–68) by RANTES(3–68). THP-1 cells were first stimulated with buffer or different concentrations of recombinant RANTES (1–68) or RANTES(3–68). Results represent the mean±SEM (three or more independent experiments) increase in $[Ca^{2+}]_i$ in response to 30 ng/ml of intact recombinant RANTES as a second stimulus.

In $Ca^{2+}$-mobilization experiments with THP-1 cells (FIG. 4), 30 ng/ml of intact RANTES could desensitize for the effect of 30 ng/ml of intact RANTES for 39±5%. About ten-fold higher concentrations of RANTES(3–68) were necessary to obtain the same amount of desensitization. However, at 300 ng/ml, RANTES(3–68) by itself gave a significant $Ca^{2+}$-response. This $Ca^{2+}$-response was comparable to the response obtained with 30 ng/ml of intact RANTES.

TABLE I

RANTES(3-68) desensitizes monocyte chemotaxis induced by RANTES(1-68)[1]

| Chemokine(ng/ml) | | | | | | | |
|---|---|---|---|---|---|---|---|
| Lower well RANTES (1-68) | Upper well RANTES (3-68) | Chemotactic response (CI) | | | | | % inhibition |
| | | A | B | C | D | mean ± SEM | mean ± SEM |
| 300 | 1000 | 12.5 | 7.5 | 27.5 | 50.5 | 25 ± 10 | 67 ± 8 |
|  | 300 | 22.0 | 20.5 | 72.5 | 79.5 | 49 ± 16 | 31 ± 13 |
|  | 0 | 41.0 | 46.0 | 71.5 | 97.0 | 64 ± 13 | 0 |
| 100 | 1000 | 4.0 | 3.0 | 13.5 | 11.0 | 8 ± 3 | 82 ± 4 |
|  | 300 | 7.5 | 7.0 | 29.0 | 33.0 | 19 ± 7 | 53 ± 11 |
|  | 0 | 24.0 | 21.5 | 50.0 | 44.5 | 35 ± 7 | 0 |

[1]Results represent the chemotactic index (C.I.) of four (A to D) independent experiments (including mean ± SEM) and the percentage (%) inhibition (mean ± SEM of the % inhibition of the four experiments) of the chemotactic response towards RANTES(1-68) after preincubation of the THP-1 cells with inactive RANTES(3-68) or buffer.

Impaired Chemotactic Activity of RANTES(3–68) for Human Monocytes and Eosinophils In Table II the chemotactic potency of natural RANTES (3–68) is compared with that of the monocyte chemotactic protein MCP-3 and intact RANTES(1–68). It can be seen that MCP-3 and RANTES(1–68) are still chemotactic for freshly isolated peripheral blood monocytes at 3 ng/ml and 30 ng/ml, respectively, whereas natural RANTES(3–68) remained inactive at 100 ng/ml.

The reduced chemotactic potency of this natural variant, was confirmed with recombinant RANTES(3–68). Although weakly chemotactic for monocytes (at 1 µg/ml), purified recombinant RANTES(3–68) showed a specific activity which is 10-fold lower than that of intact recombinant RANTES.

Figure 5:
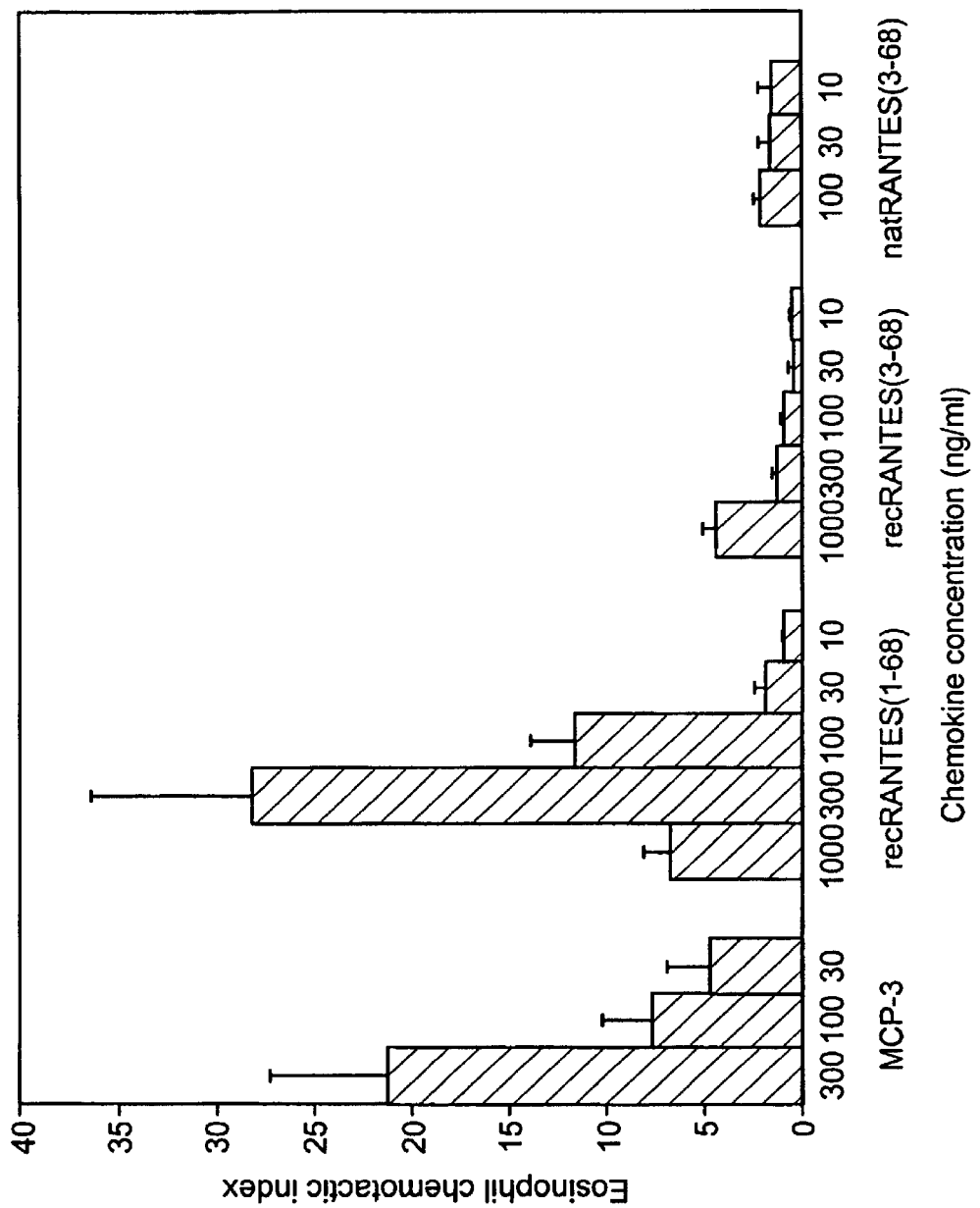
FIG. 5: Comparison of the chemotactic potency of truncated RANTES(3–68) with intact RANTES(1–68). The eosinophilic granulocyte chemotactic activity of natural (nat) and recombinant (rec) truncated RANTES, intact RANTES and synthetic MCP-3 was determined in the microchamber assay. Results represent the mean chemotactic index (CI)±SEM of two or more independent experiments (each performed in triplicate).

Finally, the chemotactic potency of RANTES(3–68) was verified on human eosinophils, which were still responsive to 100 ng/ml of intact RANTES and 30 ng/ml of MCP-3 (FIG. 5). Similar to monocytes, eosinophil migration was only stimulated by RANTES(3–68) at 1 µg/ml.

TABLE II

Comparison of the monocyte chemotactic activity of RANTES(3-68) with RANTES(1-68) and MCP-3

| conc. (ng/ml) | MCP-3 | natRANTES (3-68) | recRANTES (1-68) | recRANTES (3-68) |
|---|---|---|---|---|
| 1000 | —[b] | — | 3.6 ± 0.8(6) | 3.3(1) |
| 300 | 6.0 ± 1.2(6) | — | — | — |
| 100 | — | 1.1 ± 0.1(3) | 3.3 ± 0.4(6) | 1.0(1) |
| 30 | 6.9 ± 1.0(6) | 1.7 ± 0.2(3) | — | — |
| 10 | — | 1.9 ± 0.6(3) | 1.9 ± 0.4(6) | <1.0(1) |
| 3 | 4.1 ± 0.4(6) | — | — | — |

[a] mean chemotactic index (CI) ± SEM (n) on freshly isolated peripheral blood monocytes.
[b] not determined RANTES(3–68) Signals and Desensitizes for RANTES (1–68) Through CCR5, but not Through CCR1 and CCR3

To explain the reduced chemotactic activity of RANTES (3–68), the capacity of this chemokine variant to bind and signal through the known receptors used by RANTES was verified.

HOS cells transfected with the chemokine receptors CCR1, CCR3 or CCR5 were used in a signaling assay measuring increases in the intracellular calcium concentration. At concentrations up to 300 ng/ml, RANTES(3–68) did not increase the $[Ca^{2+}]_i$ in HOS cells transfected with CCR1 (Table III) or CCR3 (data not shown), whereas 30 ng/ml and 100 ng/ml of intact RANTES was sufficient to induce an increase in $[Ca^{2+}]_i$ in CCR1 and CCR3 transfectants, respectively.

Figure 6:
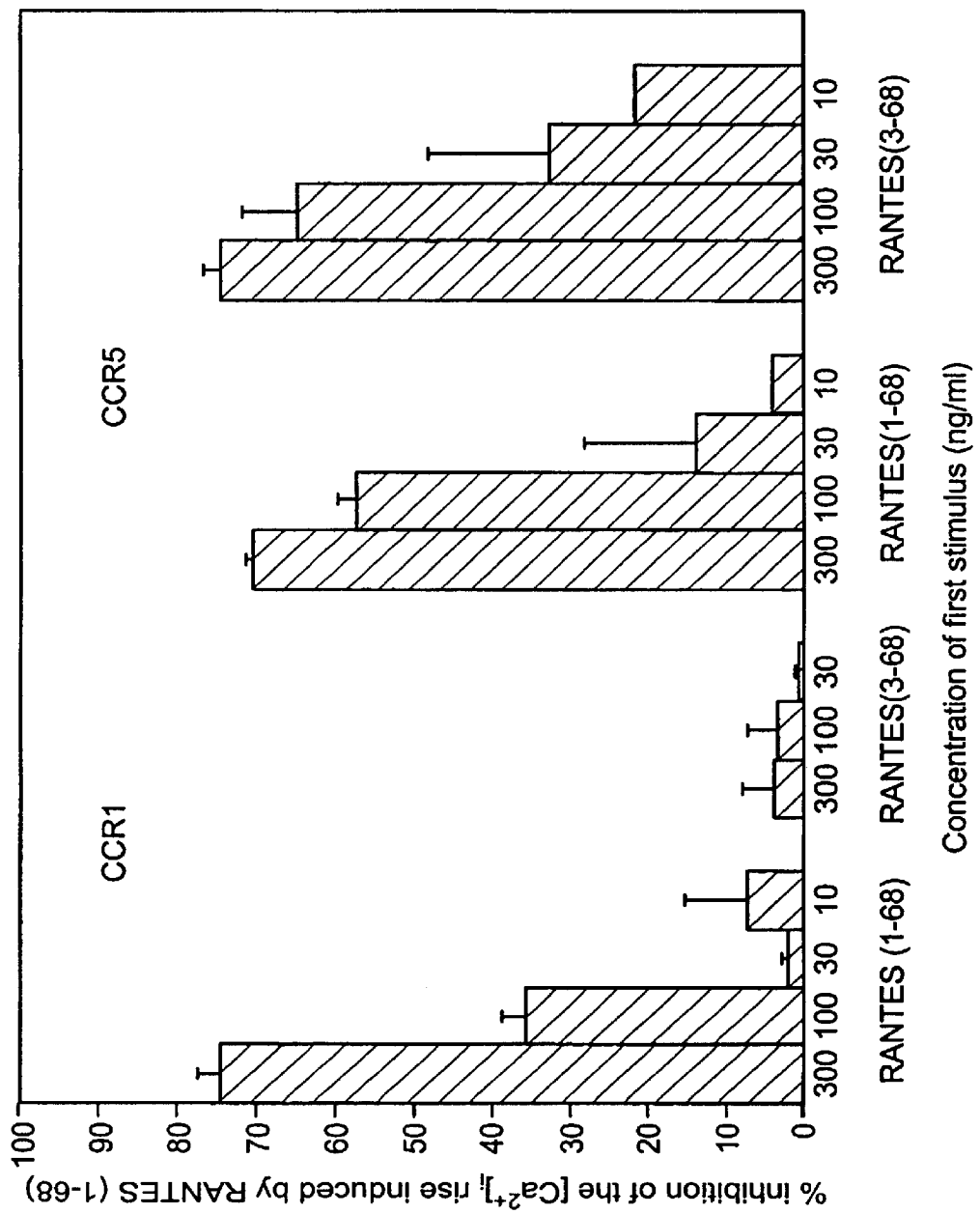
FIG. 6: Desensitization of calcium mobilization by intact RANTES in CCR transfectants. Calcium mobilization experiments were performed in HOS cells transfected with CD4 and the CC chemokine receptors CCR1 or CCR5. Cells were first stimulated with different concentrations of intact or truncated RANTES, followed by stimulation with 100 ng/ml of intact RANTES. The percentage inhibition of the $[Ca^{2+}]_i$ increase induced by the second stimulus is shown. This percentage was calculated by comparing the response of 100 ng/ml of intact RANTES after addition of RANTES (1–68) or RANTES(3–68) with the reponse after stimulation with buffer (100%). Results represent the mean percentage inhibition±SEM of two or more experiments.
Figure 7:
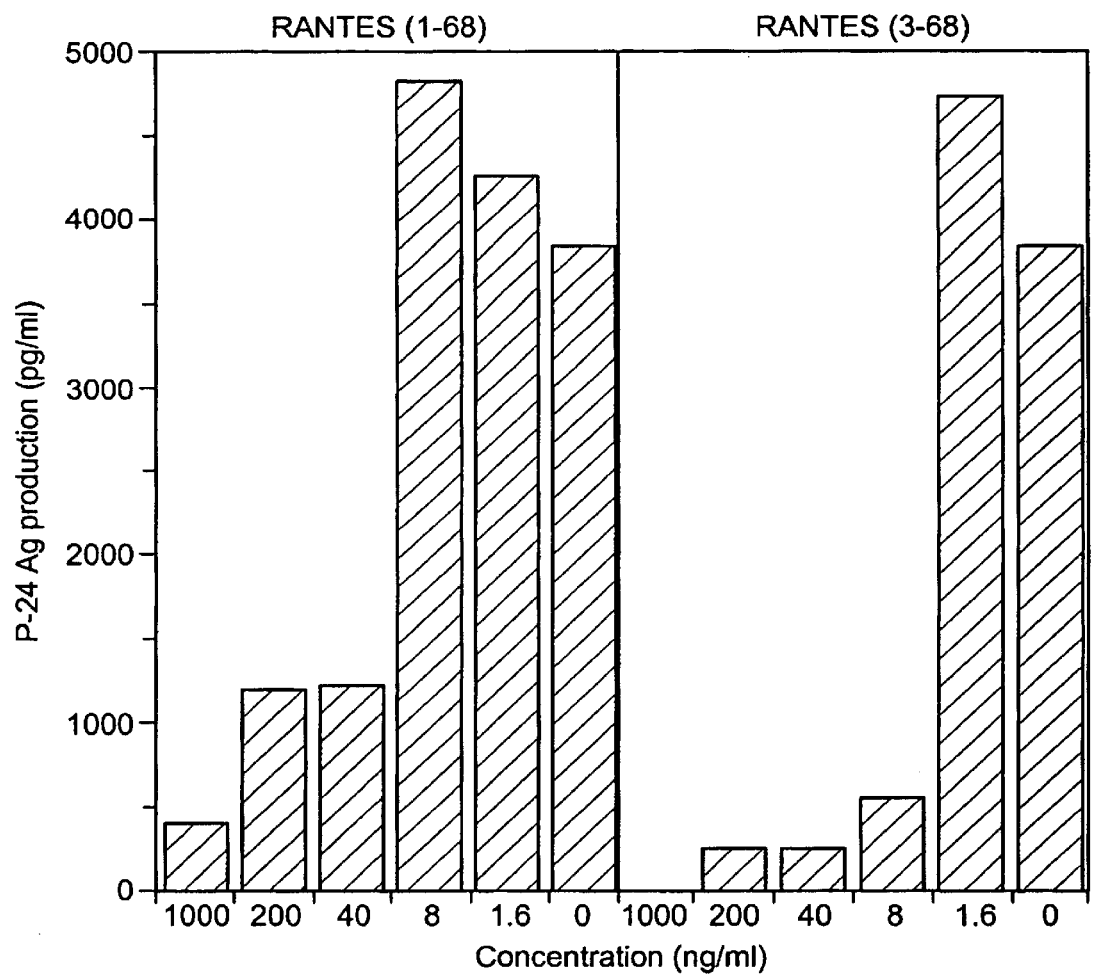
FIG. 7: Potent inhibitory effect of RANTES (3–68) on infection of mononuclear cells by HIV-1. PHA-activated PBMC were infected with M-tropic HIV-1 Ba-L strain in the presence of various concentrations of RANTES (1–68) or RANTES (3–68) (0 to 1,000 ng/ml added at the time of infection). After ten days virus yields were monitored in the cell supernatant by a p-24 Ag ELISA (one representative experiment out of four is shown).

However, both intact and truncated RANTES were able to induce a significant rise in $[Ca^{2+}]_i$ in CCR5 transfectants at 30 ng/ml. Furthermore, by pre-incubation of CCR5-transfected cells with a 3 to 10-fold excess of either RANTES(3–68) or intact RANTES, an equal inhibition (about 75%) of the $[Ca^{2+}]_i$ rise by a subsequent challenge with intact RANTES (100 ng/ml) was obtained (FIG. 6).

In contrast, 300 ng/ml of RANTES(3–68) only marginally desensitized the calcium response of CCR1 and CCR3-transfected cells to 100 ng/ml of intact RANTES, whereas a 3-fold excess of intact RANTES as first stimulus almost completely inhibited the $[Ca^{2+}]_i$ rise in these cells by subsequent RANTES(1–68). It must be concluded that removal of two $NH_2$-terminal residues from RANTES has a significant impact on signal transduction in that the chemokine receptors CCR1 and CCR3 are no longer functionally recognized. Therefore, the impaired chemotactic potency of RANTES(3–68) can be explained by its inability to function through CCR1 and CCR3. In contrast, RANTES(3–68) fully retained the CCR5 signalling characteristic of intact RANTES. RANTES(3–68) can be anti-inflammatory by competing with intact RANTES, but may still function as an HIV-inhibitor by retaining its capacity to bind CCR5.

TABLE III

Calcium mobilization by RANTES forms in CCR1 and CCR5 transfectants

| chemokine | conc. (ng/ml) | increase in $[Ca^{2+}]_i$ (nM)[a] CCR1 | CCR5 |
|---|---|---|---|
| RANTES(1-68) | 300 | 133 ± 5(3) | 96 ± 1(2) |
|  | 100 | 100 ± 28(3) | 60 ± 4(2) |
|  | 30 | 25 ± 8(3) | 24 ± 2(2) |
|  | 10 | <15(2) | <15(1) |
| RANTES(3-68) | 300 | 19 ± 9(3) | 119 ± 5(2) |
|  | 100 | <15 ± 0(3) | 76 ± 4(2) |
|  | 30 | <15(2) | 56 ± 13(2) |
|  | 10 |  | <15(1) |

[a] the mean increase in $[Ca^{2+}]_i$ in nM ± SEM of two or more independent experiments is shown.

Inhibition of CC Chemokine-induced Chemotaxis by RANTES(3–68) in Human Monocytic Cells To verify whether inhibition of CC chemokine signaling by RANTES(3–68) also occurred in monocytic cells, inhibition experiments were conducted in THP-1 cells. It was evidenced that RANTES(3–68) showed a 10-fold reduction in potency to increase the $[Ca^{2+}]_i$ in monocytic cells compared to intact RANTES (data not shown). In addition, the chemotactic effect of intact RANTES (30 ng/ml) on monocytic cells was inhibited (71%) by incubating the test cells with 300 ng/ml RANTES(3–68) as shown in Table IV.

Furthermore, RANTES(3–68) reduced the chemotactic response to other CC chemokines, including monocyte chemotactic protein-3 (MCP-3) (67%), macrophage inflammatory protein-1a (MIP-1α) (61%) and MIP-1β (80%).

This illustrates that RANTES(3–68) functions as a broad spectrum inhibitor of monocytic cell migration induced by other CC chemokines.

TABLE IV

Inhibition of monocytic cell chemotaxis towards CC chemokines by RANTES(3-68)

| chemokine[a] | conc. (ng/ml) | buffer[b,c] | inhibition of THP-1 cell chemotaxis RANTES(3-68)[b,c] | % inhibition[d] |
|---|---|---|---|---|
| RANTES | 30 | 19.0 ± 6.6 | 3.7 ± 0.6 | 71 ± 16 |
| MCP-3 | 30 | 48.5 ± 9.3 | 24.9 ± 2.0 | 45 ± 10 |
| MCP-3 | 3 | 7.6 ± 2.5 | 3.1 ± 0.8 | 67 ± 13 |
| MIP-1α | 30 | 6.2 ± 2.4 | 3.0 ± 1.1 | 61 ± 22 |
| MIP-1β | 300 | 4.3 ± 1.0 | 1.9 ± 0.6 | 80 ± 12 |
| control |  | 1.5 ± 0.5 | 1.0 ± 0.5 |  |

[a] RANTES, MCP-3, MIP-1α, MIP-1β and buffer were added as chemoattractants to the lower wells of the microchamber.
[b] the upper wells of the microchamber were filled with THP-1 cells preincubated (10 min, 37° C.) with 300 ng/ml RANTES(3-68) or with buffer.
[c] mean CI ± SEM of four independent experiments.
[d] inhibition of migration induced by intact chemokines in the presence of RANTES(3-68) at 300 ng/ml.

CD26-specific Truncation of RANTES is Necessary for Its Antiviral Activity.

Figure 8A:
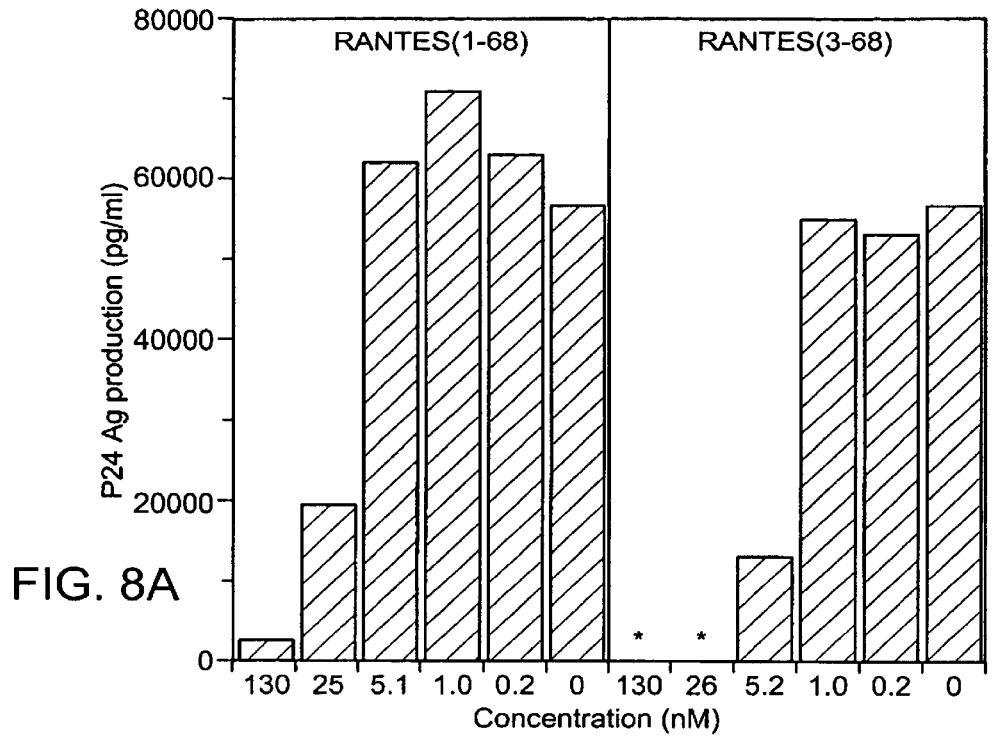
FIG. 8: Effects of RANTES(1–68) and RANTES(3–68) on infection by the HIV-1 SF162 strain in PHA-activated PBMC. Virus yields were monitored 10 days after infection by a p24 Ag ELISA on the cell supernatant. Results of a representative experiment out of three are shown. * Under the detection limit of the p24 Ag ELISA (<5 pg/ml).
Figure 8B:
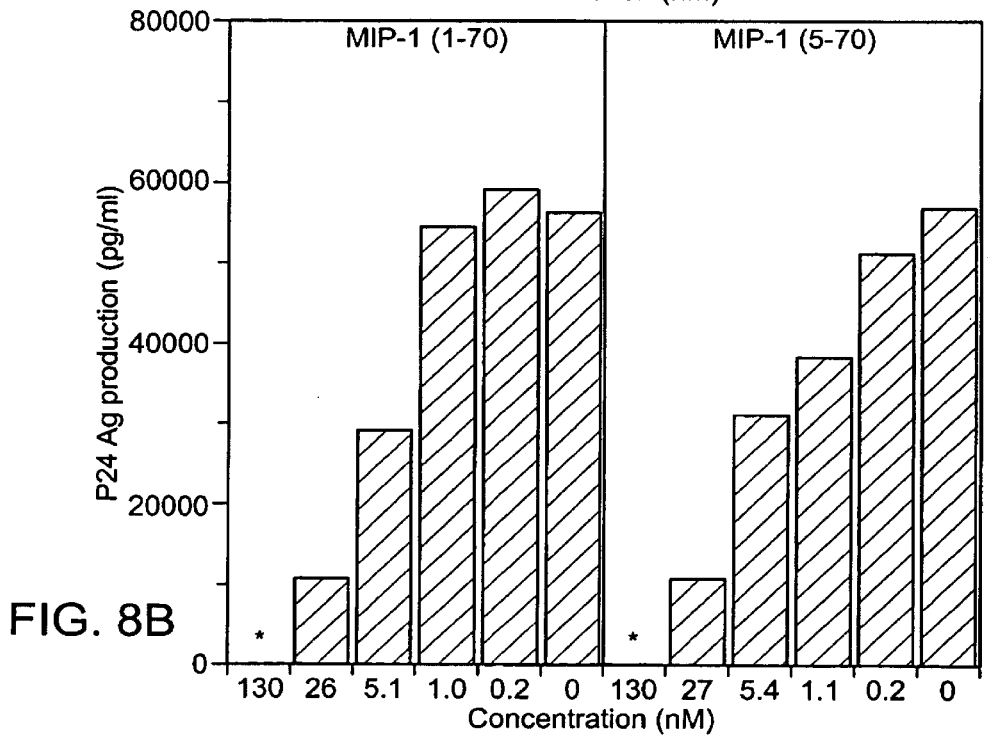

The effects of the different forms of RANTES were first evaluated against two different M-tropic HIV-1 strains (BaL and SF162) in human PBMC derived from healthy blood donors. The $IC_{50}$ of the intact RANTES(1–68) against the BaL strain was 3.4 nM and for RANTES(3–68) the $IC_{50}$ was 0.39 nM. The $IC_{90}$ value for RANTES(1–68) was 71 nM, which was about 10-fold the $IC_{90}$ for RANTES(3–68). Against the SF162 strain when evaluated in PBMC, RANTES(1–68) ($IC_{50}$: 23 nM; $IC_{90}$: 95 nM) was more than 10-fold less active than RANTES(3–68) ($IC_{50}$: 2 nM; $IC_{90}$: 8.2 nM) (Table V). The concentration-dependent effects of both chemokines at concentrations ranging from 133 down to 0.2 nM against HIV-1 SF162 replication in PBMC are shown in FIG. 8. A concentration of 5.2 nM RANTES(3–68) was clearly effective in reducing virus replication, whereas RANTES(1–68) was inactive at this concentration. No difference in antiviral activity was noticed between intact RANTES obtained from PeproTech or R&D Systems.

The striking difference in antiviral activity between the two forms of RANTES became even more apparent when tested in the human CCR5 transfected cells. In U78.CD4.CCR5 cells, the $IC_{50}$ for RANTES(1–68) and RANTES(3–68) against the BaL strain was 21 nM and 0.65 nM, respectively. The $IC_{90}$ for RANTES(1–68) was more than 133 nM, whereas the $IC_{90}$ for RANTES(3–68) was 63 nM. Also in Table V, it is shown that RANTES(1–68) was virtually inactive in the HOS.CD4.CCR5 cells ($IC_{50}$>133 nM), whereas RANTES(3–68) is a potent inhibitor of HIV-1 BaL replication in these cells ($IC_{50}$: 5.5 nM). However, no $IC_{90}$ values were reached for both forms of RANTES in these cells.

The Antiviral Activity of RANTES is Dependent on the Presence of Membrane Bound or Soluble CD26 (sCD26)

Figure 9:
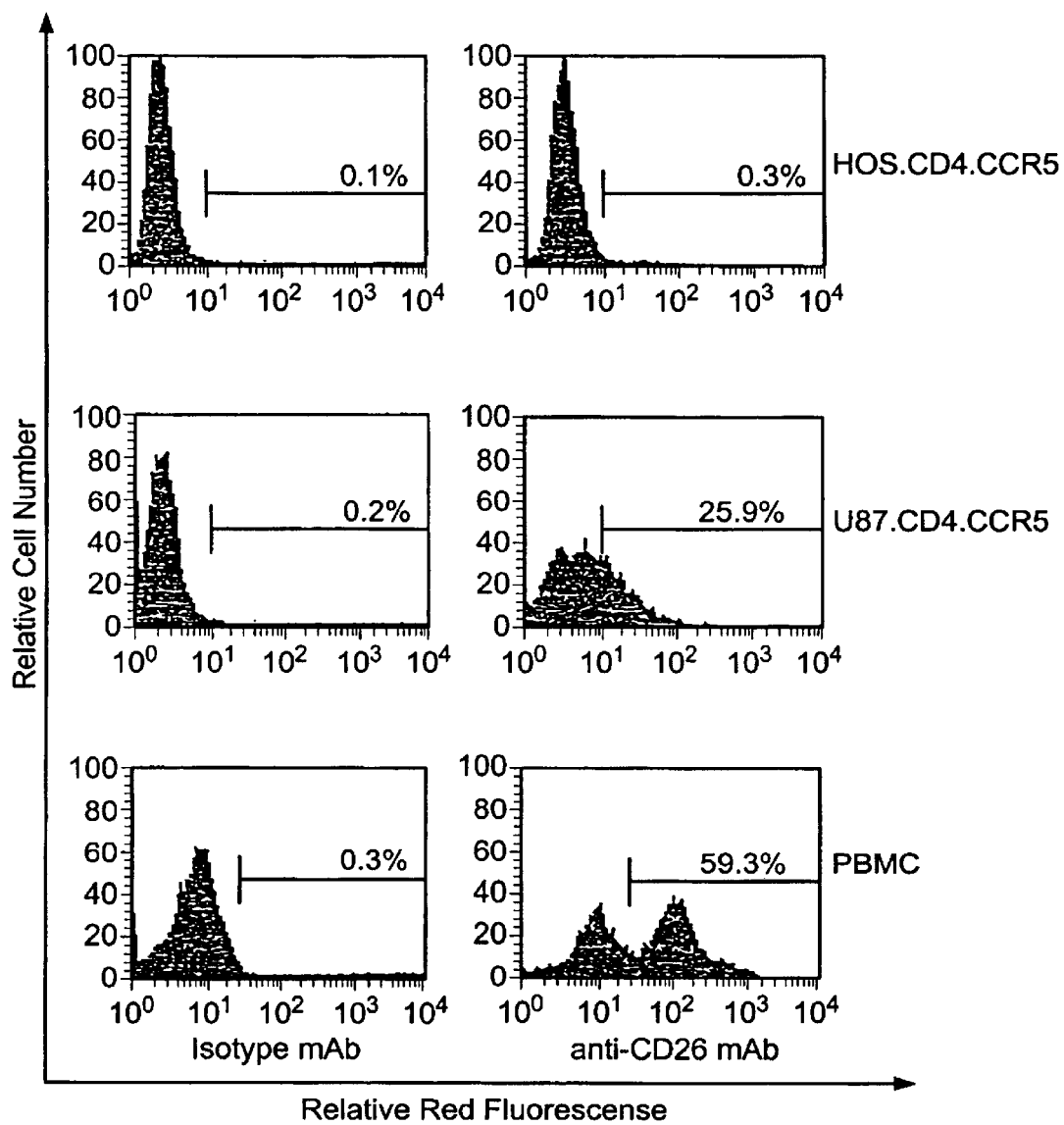
FIG. 9: Expression of CD26 on HOS.CD4.CCR5 cells, U87.CD4.CCR5 cells and freshly-isolated PBMC. The percentage (%) of CD26 positive cells is indicated in each histogram.

The CD26 expression on the two different CCR5-transfected cell lines and on freshly isolated PBMC was evaluated. HOS transfectants were negative for CD26 expression as determined by flow cytometric analysis, whereas U87 transfectants stained weakly but significantly positive with the anti-CD26 mAb (FIG. 9). In addition, a subpopulation of freshly isolated PMBC was found to be strongly positive for CD26 expression (FIG. 9).

Figure 10:
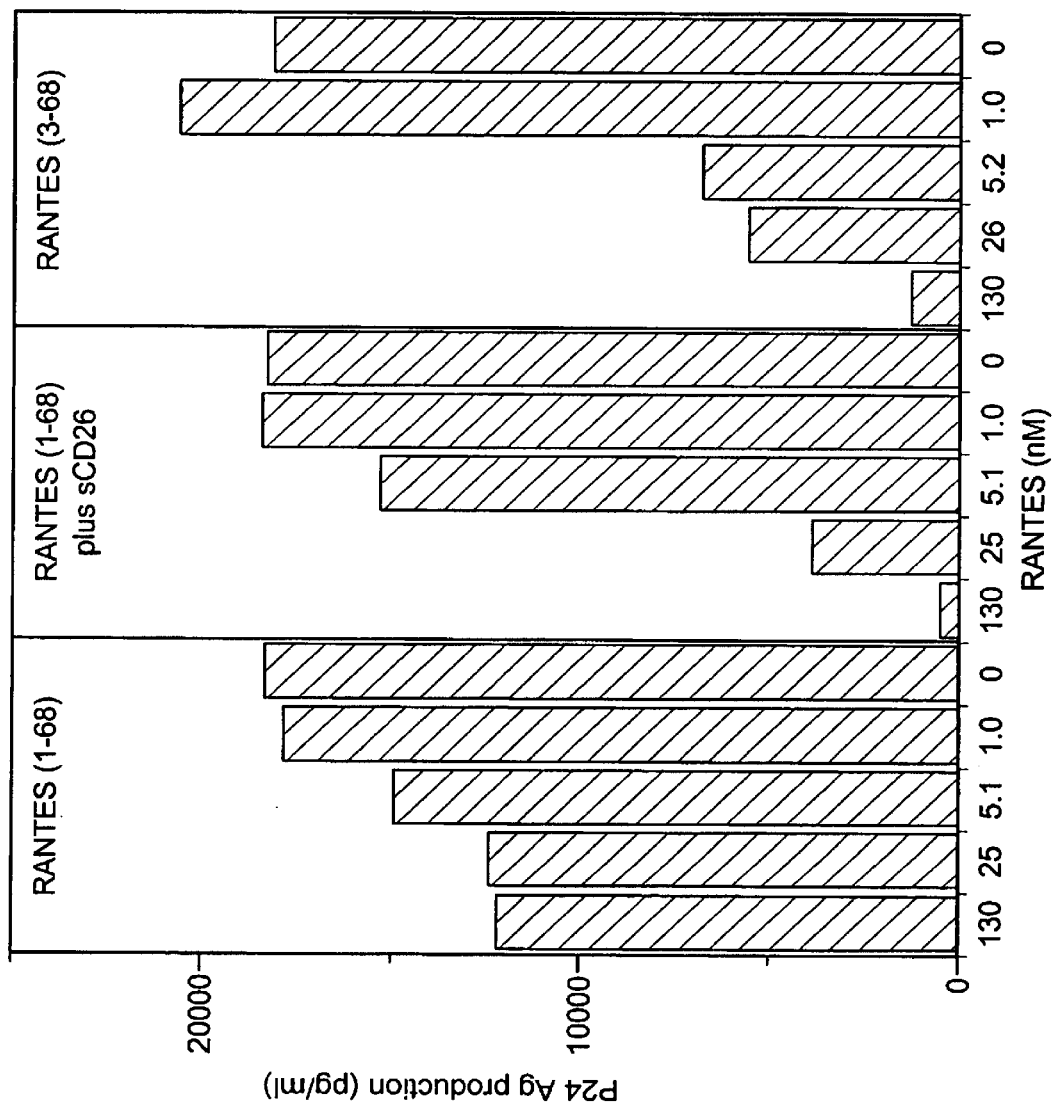
FIG. 10: Effects of RANTES(1–68), RANTES(1–68) plus sCD26 (50 U/L), and RANTES(3–68) on infection of HOS.CD4.CCR5 cells by the HIV-1 BaL strain. Virus yields were monitored in the cell supernatant 8 days after infection by a p24Ag ELISA. Results of a representative experiment out of three is shown.

The concentration-dependent effect of RANTES(1–68) and RANTES(3–68) on viral p24 Ag production by the BaL strain in HOS.CD4.CCR5 transfected cells in presence of sCD26 is shown in FIG. 10. Addition of sCD26, together with RANTES(1–68) at the start of the HIV infection, significantly enhanced the antiviral activity of the intact RANTES in HOS.CD4.CCR5 cells. When sCD26 at 50 U/l was added together with RANTES, an $IC_{50}$ of 13 nM of RANTES was obtained. The addition of sCD26 alone had no effect on virus replication. The addition of sCD26 to RANTES(3–68) did also not change the antiviral activity of RANTES(3–68) (data not shown). Thus, the presence of CD26 is essential for intact RANTES to become antivirally active.

Amino Terminal Truncation of Natural MIP-1 α Does not Affect Its Anti-HIV-1 Chemotactic and $Ca^{2+}$ Mobilising Activity Since the majority of natural MIP-1α is $NH_2$ terminally truncated (four amino acids), we investigated whether this truncated MIP-1α(5–70) had an altered HIV-1 inhibitory capacity. In contrast with the results obtained for RANTES, no significant differences were detected for the $IC_{50}$ values of intact MIP-1α and MIP-1α(5–70) in PMBC or CCR5-transfected cells (Table V, FIG. 8). In addition, intact MIP-1α and truncated MIP-1α(5–70) were compared in chemotaxis and intracellular $Ca^{2+}$-mobilization assays on THP-1 monocytic cells. Table VI demonstrates that the minimal effective dose of MIP-1α(5–70) inducing a rise in the $[Ca^{2+}]_i$ was only slightly lower than intact MIP-1α. Furthermore, although maximal migration obtained with 0.13 nM in the chemotaxis assay was higher for intact MIP-1α, the minimal affective concentrations of both MP-1α isoforms were rather similar. Taken together, it must be concluded that $NH_2$ terminal processing of MIP-1α in contrast to RANTES, only minimally weakens its inflammatory and anti-HIV-1 activity.

TABLE V

Anti-HIV-1 activity of RANTES and MIP-1α in PHA-stimulated PMBC, U87.CD4.CCR5 cells.

|  | RANTES(1-68) | | RANTES(3-68) | | MIP-1α(1-70) | | MIP-1α(5-70) | |
| --- | --- | --- | --- | --- | --- | --- | --- | --- |
|  | $IC_{50}$ | $IC_{90}$ | $IC_{50}$ | $IC_{90}$ | $IC_{50}$ | $IC_{90}$ | $IC_{50}$ | $IC_{90}$ |
| PMBC BaL | 3.4 | 71 | 039 | 6.9 | 1.9 | 62 | 1.6 | 13 |
| SF162 | 23 | 95 | 2.0 | 8.2 | 3.1 | 30 | 3.6 | 32 |
| U87.CD4.CCR5 BaL | 21 | >130 | 0.65 | 63 | ND | ND | ND | ND |
| HOS.CD4.CCR5 BaL | >130 | >130 | 5.5 | >130 | 32 | >130 | 21 | >130 |

Virus yield was monitored in the cell-free supernatant 8–12 days after infection by viral p24 Ag ELISA. The mean $IC_{50}$s and $IC_{90}$s (in nM) are shown. The data represent the means of two to four independent experiments. The value marked by ">130" indicates that 50% or 90% inhibition is not achieved at 130 nM. ND, not done.

TABLE VI

Lack of difference in biological potency between intact and truncated MIP-1α.

|  | Chemotaxis* | | Increase in $[Ca^{2+}]_i$† | |
| --- | --- | --- | --- | --- |
| Chemokine | nM | C.I | nM | nM $[Ca^{2+}]_i$ |
| MIP-1α(1-70) | 1.3 | 8.5 ± 3.3 | 3.9 | 240/195 |
|  | 0.13 | 22.2 ± 4.4 | 0.39 | 120/130 |
|  | 0.013 | 5.7 ± 1.6 | 0.34 | 30/14 |
|  | 0.0013 | 4.0 ± 3.1 |  |  |

TABLE VI-continued

Lack of difference in biological potency between intact and truncated MIP-1α.

| Chemokine | Chemotaxis* | | Increase in $[Ca^{2+}]_i$† | |
|---|---|---|---|---|
| | nM | C.I | nM | nM $[Ca^{2+}]_i$ |
| MIP-1α(5-70) | 1.3 | 14.2 ± 0.4 | 4.0 | 196/178 |
| | 0.13 | 11.4 ± 2.9 | 0.4 | 71/33 |
| | 0.013 | 3.8 ± 1.4 | 0.04 | 10/<10 |
| | 0.0013 | 2.1 ± 0.6 | | |

*Migration of monocyte THP-1 cells through 5.0 μm pores in the microchamber. Resuls are mean ± of three independent experiments.
†Detection of the $[Ca^{2+}]_i$ increase in THP-1 cells. Results of two independent experiments are shown.

REFERENCES

Baggiolini M. et al., *Ann. Rev. Immunol.*, 55, 97–179, 1994.
Baggiolini M. et al., *Ann. Rev. Immunol.*, 15, 675–705, 1997.
Clark-Lewis I. et al., *J. Biol. Chem.*, 266, 23128–23134, 1991.
De Meester I. et al., *J. Immunol. Methods* 189, 99–10526, 1996.
Deng H. et al., *Nature.*, 381, 661–666, 1996.
Gong J. et al. *J. Exp. Med.*, 181, 631–640, 1995.
Gong J. et al., *J. Biol. Chem.* 271, 10521–10527, 1996.
Grynkiewicz G. et al., *J. Biol. Chem.*, 260, 3440, 1985.
Proost P. et al., *Biochemistry*, 32, 10170–10177, 1993a.
Proost P. et al., *J. Immunol.*, 150, 1000–1010, 1993.
Proost P. et al., *Cytokine*, 7, 97–104, 1995.
Proost P. et al., *Methods: A companion to Methods in Enzymol.*, 10, 82, 1996.
Proudfoot A. E. et al., *J. Biol. Chem.*, 271, 2599–2603, 1996.
Sambrook et al, Molecular Cloning: A laboratory Manual Cold Spring Harbor Laboratory, Cold Spring Harbor, N.Y., 1989.
Schall T. J. et al., *J. Immunol.*, 141, 1918–1025, 1988.
Schols D. et al., *J. Exp. Med.*, 186, 1383–1388, 1997.
Sozzani S. et al., *J. Immunol.*, 152, 3615, 1994.
Taub D. et al., *Cytokine & Growth Factor Reviews*, 7, 335–76, 1996.
Van Damme J. et al., *Eur. J. Biochem.*, 181, 337–344, 1989.
Van Damme J. et al., *Eur. J. Immunol.*, 20, 2113–8, 1990.
Van Damme J. et al., *J. Exp. Med.*, 176, 59, 1992.
Walz A. et al., *Biochem. Biophys. Res. Commun.*, 159, 969–75, 1989.
Wuyts A., et al., *Biochemistry*, 36, 2716–2723, 1997.

What is claimed is:

1. An isolated amino-terminally truncated RANTES polypeptide consisting of residues 3–68 of a RANTES polypeptide according to SEQ ID NO:1, wherein the truncated RANTES polypeptide lacks $NH_2$-terminal amino acid residues 1–2 and has the ability to inhibit monocyte cell chemotaxis towards MCP-3, MIP-1α and MIP-1β, and has CCR5 agonistic activity.

2. The isolated amino-terminally truncated RANTES of claim 1, wherein the truncated RANTES polypeptide is in glycosylated form.

3. A pharmaceutical composition comprising an isolated truncated RANTES polypeptide according to claim 1, wherein the composition comprises one or more pharmaceutically acceptable carriers and/or excipients.

4. The pharmaceutical composition according to claim 3, wherein the isolated truncated RANTES polypeptide is in glycosylated form.

* * * * *